United States Patent [19]

Harper

[11] Patent Number: 5,309,185
[45] Date of Patent: May 3, 1994

[54] APPARATUS AND METHOD FOR OBJECTIVE QUANTITATIVE ASSESSMENT OF HUMAN OCULAR COORDINATION

[76] Inventor: Gilberto B. Harper, 2724 Sandover Ct., Bonita, Calif. 91902

[21] Appl. No.: 894,830

[22] Filed: Jun. 8, 1992

[51] Int. Cl.$^5$ .............................................. A61B 3/08
[52] U.S. Cl. .................................. 351/202; 351/213; 351/215
[58] Field of Search .............. 351/201, 202, 203, 211, 351/213, 214, 215, 220, 222, 224, 233, 243, 246, 237

[56] References Cited

U.S. PATENT DOCUMENTS

| | | | |
|---|---|---|---|
| Re. 28,921 | 8/1976 | Haines et al. | 351/224 |
| 1,292,671 | 1/1919 | Allen et al. | 351/202 |
| 1,437,776 | 12/1922 | Reese et al. | |
| 2,526,513 | 11/1950 | Grether | 346/108 |
| 3,025,754 | 3/1962 | Mirsky | 351/202 |
| 3,486,813 | 12/1969 | Johnston | 351/239 |
| 3,547,428 | 12/1970 | Weisfield | 351/201 |
| 3,718,386 | 2/1973 | Lynn et al. | 351/246 |
| 3,724,933 | 4/1973 | Mohon et al. | 351/243 |
| 3,737,217 | 6/1973 | Haines et al. | 351/224 |
| 3,861,790 | 1/1975 | Tamura | 351/237 |
| 3,874,774 | 4/1975 | Humphrey | 351/233 |
| 3,905,688 | 9/1975 | Decker et al. | 351/237 |

OTHER PUBLICATIONS

Michaels, *Visual Optics and Refraction: A Clinical Approach* (3rd edn., 1985), pp. 373-380.
Newell, *Opthalmology: Principles and Concepts* (6th edn., 1986) pp. 399-404.
Schapero et al., *Dictionary of Visual Science* (2nd edn., 1968), pp. 327, 539-541.
Shulman, "The Strabismometer and its Function", *The Optometric Weekly*, (Sep. 12, 1987), pp. 1747-1749, 1773.

*Primary Examiner*—Loha Ben
*Attorney, Agent, or Firm*—Brown, Martin, Haller & McClain

[57] ABSTRACT

Apparatus for objective quantitative assessment of human ocular coordination is disclosed, including a first pair of transparent image filters (commonly as spectacles) which transmit different visual images, a projector to produce a pair of visual images; a viewing surface on which the visual images are separately viewed by a patient; controls to allow the patient to move the images relative to each other; and scales for quantitatively determining the spatial relationship between the visual images on the viewing surface which results from the movement by the patient. Also disclosed is a method for objective quantitative assessment of human ocular coordination by use of such apparatus. The apparatus may include a second pair of transparent image filters corresponding to the image transmitted by one respective filter of the first pair through which is projecting each of the pair of images onto the viewing surface. The filters may differ from each other in their ability to transmit colored light (such as complimentary colors such as red and green light) or in their ability to transmit polarized light. The invention is particularly useful is the assessment of phorias and ocular deviation, and eliminates subjective assessment of a patient's narration of his or her visual observations, especially in the examination of children or other inarticulate patients.

39 Claims, 5 Drawing Sheets

APPARATUS AND METHOD FOR OBJECTIVE QUANTITATIVE ASSESSMENT OF HUMAN OCULAR COORDINATION

BACKGROUND OF THE INVENTION

1. Field of the Invention

The invention herein relates to the assessment of human ocular coordination for the diagnosis of phorias for treatment of dysfunctional phorias.

2. Background of the Prior Art

Eye care professionals, such as ophthalmologists and optometrists, routinely examine patients to assess the ocular coordination of the patient's eyes. Most people possess the ability innately to bring into satisfactory alignment the individual binocular vision images registered by each of the person's eyes. However, a substantial number of individuals are afflicted with various physical conditions which limit or prevent proper binocular vision. A principal class of such conditions, particularly those which pertain to horizontal coordination of images, are phorias. These types of visual conditions have long been described in the literature; see, for instance, Newell, *Ophthalmology: Principles and Concepts* (6th ed.; 1986), Chapter 21 and Michaels, *Visual Optics and Refraction: A Clinical Approach* (3rd ed.; 1985), Chapter 18. While some phorias, such as orthophoria or exophoria, are either considered good or at least not normally a significant dysfunction, others, such as esophoria, are considered to constitute cosmetic and/or functional dysfunctions. Among the effects and elements involved in such dysfunctional conditions are poor or non-existent depth perception, unequal muscle balance, dominance of one eye's image over that of the other eye, and inability to make independent vertical or horizontal coordination of images.

There have in the past been devices designed to enable an eye care professional to attempt to assess a patient's ocular coordination. Several types of devices commonly referred to as phorometers were designed and used; some of these are referred to in the aforesaid Michaels text, Chapter 18, and others are briefly described in Schapero et al., *Dictionary of Visual Science* (2nd ed.; 1968), pp. 327 and 540. A few of these devices have also incorporated means for obtaining a quantitative value for the degree of non-coordination exhibited by a patient. These, however, have been uniformly cumbersome and difficult to use for the ordinary practitioner. Consequently, while a few such devices still exist, they are for the most part found only in teaching facilities where they are operated by professors or other highly trained experts for the purpose of providing professional students with an understanding of ocular coordination conditions and abnormalities. Most such devices are very old, and they are essentially not practical for use by the regular eye care professional in routine patient assessment.

Consequently, virtually all current ocular coordination assessment by eye care professionals is done on a subjective basis. The patient is shown a succession of preformed images whose correct appearance is known to the examiner. The patient is then asked to state verbally what he or she sees while viewing the image. From the patient's verbal description, the examiner can make a subjective assessment as to whether the patient is seeing the image correctly or to what degree the patient's view of the image appears to differ from the correct appearance of the image. Needless to say, this type of assessment suffers from a number of deficiencies.

1. Most importantly, the examiner's assessment is wholly dependent upon the ability of the patient to express his or her view of the image verbally and in complete and appropriate detail. Thus the examination is severely limited when the patient is inarticulate or unable to express his or her thoughts accurately (such as where the patient is a foreign language speaking person not fluent in the examiner's language). Of course, the method fails completely where the patient is unable to express a coherent description of what he or she sees, as is the case in attempting to examine infants, small children or the developmentally immature.

2. Even where the patient is able to provide a reasonably comprehensive verbal description of the image he or she sees, establishment of a standard diagnosis is still very difficult or impossible, since even articulate speakers will describe the same image in different ways. This makes it very difficult for the examiner to confirm whether or not a particular patient's condition is equivalent to other predetermined levels of coordination, since the patient, while assumably seeing the same visual image, will normally not describe it in precisely the same terms as the standard definition.

3. If as is common, the eye care professional reshows the various images several times over the course of an examination, different apparent results may occur since the patient may not necessarily describe the image in identical terms each time it is repeated.

4. Even where the patient provides a good description of what he or she sees, the examiner's ability to assess that description for proper prescription of corrective lenses will still be quite subjective and only marginally quantitative. Since the patient's description of the view each time it is presented is not directly reproducible, the examiner can only get a general idea of what degree of correction is required for prescriptive lenses. The examiner must therefore, by trial and error, present to the patient a series of various corrective lenses until the patient's description of the image viewed with a particular set of corrective lenses appears to the examiner to correspond to what the examiner knows is the correct description of the image. Of course, since the final prescription is still dependent upon the examiner's subjective evaluation of the particular verbal description that the patient has articulated, which itself was subjective, the prescription may or may not in fact be optimum for that patient.

It would therefore be of great advantage to the eye care field to have available a simple and accurate objective method of providing a precise and reproducible quantitative assessment of a patient's ocular coordination. Such a device would advantageously be of equal and accurate use by eye care professionals for all types of patients, regardless of their ability to verbally express the nature of the image viewed. It would also be relatively inexpensive and of simple enough design that it could be used in medical, educational or psychological practice, not only directly by the professional but also by technical assistants having only a relatively limited degree of training. Further, such device should provide a clear and precise quantitative measurement which allows the eye care professional to unequivocally prescribe the appropriate corrective lenses for the particular patient's condition. Finally, it should be equally usable with adults and children.

SUMMARY OF THE INVENTION

In one aspect, the invention herein comprises apparatus for quantitative assessment of human ocular coordination, which comprises a first pair of transparent image filters, each filter of the first pair having means to transmit a visual image different from and mutually exclusive with the image transmitted by the other filter of the pair; means for producing a pair of visual images and displaying them on a viewing surface; the viewing surface on which the visual images are displayed to a human patient, each visual image being visible to the patient through only one respective filter of the pair of filters; means for the patient to move one of the visual images relative to the other on the viewing surface; and means for quantitatively determining the spatial relationship between the visual images on the viewing surface which results from the movement by the patient.

In another aspect, the invention herein is a method for quantitative assessment of human ocular coordination, which comprises: producing a pair of visual images; displaying the pair of visual images to a human patient on a viewing surface, each visual image being visible to the patient through a first pair of transparent image filters, each filter of the first pair having means to transmit a visual image different from and mutually exclusive with the image transmitted by the other filter of the pair such that the patient sees each image through only one respective filter of the pair of filters; providing means for the patient to move one of the visual images relative to the other on the viewing surface; and quantitatively determining the spatial relationship between the visual images on the viewing surface which results from the movement by the patient.

In preferred embodiments, the apparatus may include a second pair of transparent image filters, each filter of the pair having means to transmit a visual image different from and mutually exclusive with the image transmitted by the other filter of the pair but corresponding to the image transmitted by one respective filter of the first pair; and means for projecting each of the pair of visual images through a respective one of the second pair of filters and onto the viewing surface.

Commonly the first pair of filters is in the form of spectacles worn by the patient in which each filter is positioned in front of a respective one of the patient's eyes. In both pairs, the filters may differ from each other in their ability to transmit colored light (such as complimentary colors such as red and green light) or in their ability to transmit polarized light.

Further, there is also preferably displayed on the viewing surface a scale from which the examiner can determine the quantitative degree of lack of ocular coordination. The scale may be calibrated in appropriate units, such as prism diopters.

DETAILED DESCRIPTION AND PREFERRED EMBODIMENTS

The method and apparatus of my invention are best understood by first considering the measurements to be obtained. When a person's eyes are not properly coordinated, each focuses at a different point. The method and apparatus are based on my discovery that objective quantitative measurements of that lack of coordination can be obtained by isolating the vision of each eye from the other, simultaneously visually isolating one portion of a split image from the other, and then having the patient manipulate those two portions to form a coherent single image. The patient's ability to produce the coherent single image is then measured against a previously calibrated scale, and the amount by which the image remains split is a definitive and objective measure of the degree of the patient's lack of coordination between his or her eyes. Manipulation of the portions of the split image may be in either or both the horizontal (x coordinate) and vertical (y coordinate) directions, depending on the particular conditions which are sought to be measured. Other unique aspects of my invention will be discussed below.

Figure 1:
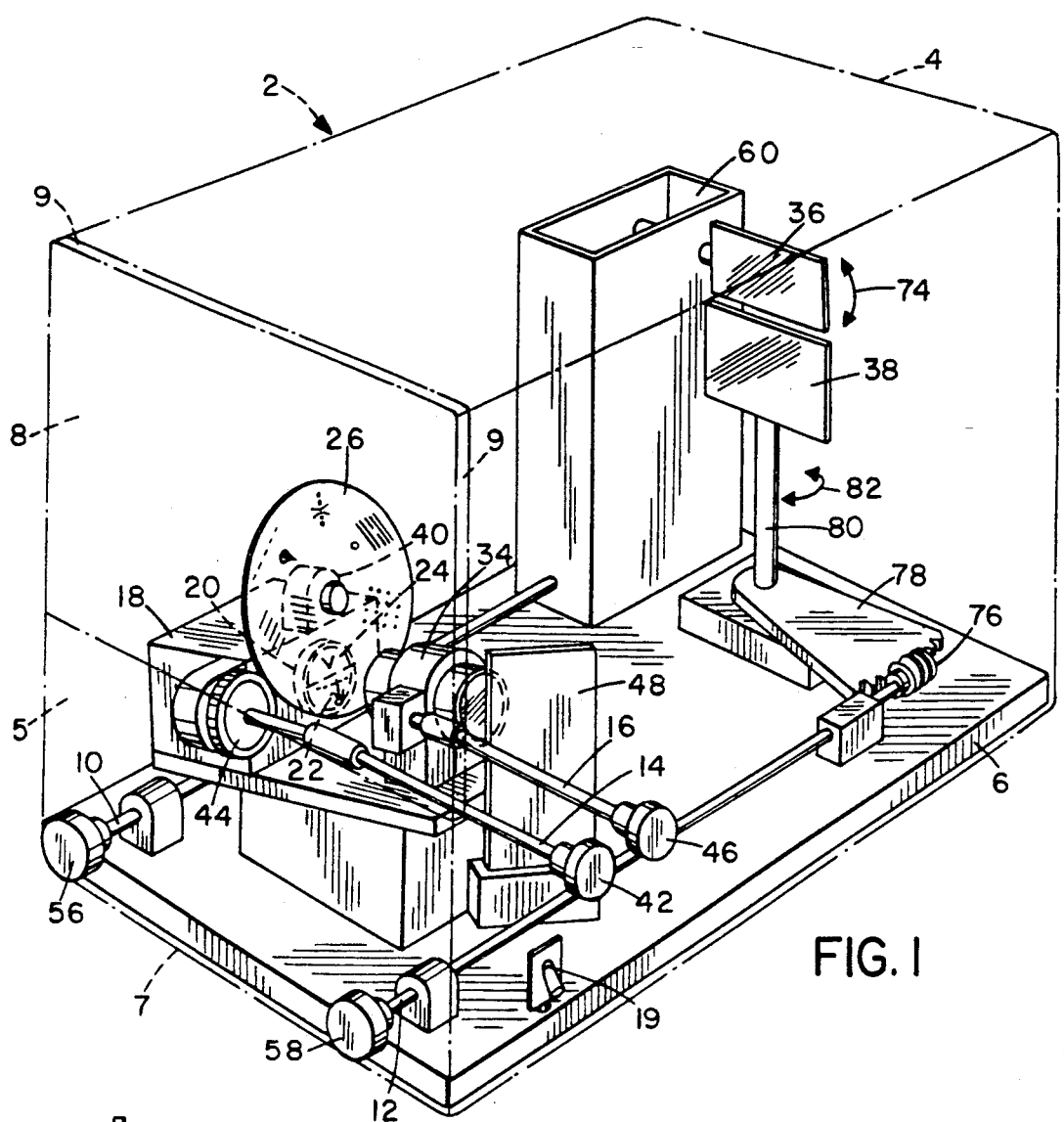
FIG. 1 is a perspective view of a typical configuration of the apparatus.
Figure 2:
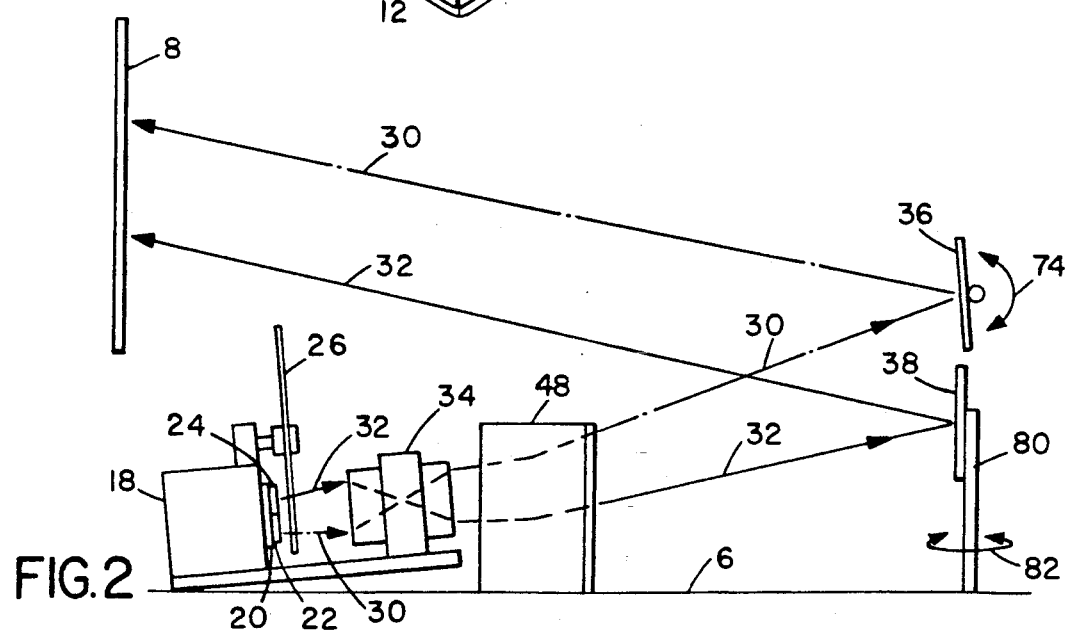
FIG. 2 is a diagram of the optical projection system of the apparatus of FIG. 1.

The method and apparatus/device of my invention can be readily understood by reference to the accompanying drawings, starting with FIGS. 1 and 2, which describe an embodiment of the device which would typically be found in an eye care professional's office.

The device generally indicated 2 is housed a box-like case 4. While this case 4 may be of any size and will be dependent upon the type of equipment housed within, commonly I have found that quite satisfactory devices are approximately the size of a table top television set or a common video monitor for a personal computer or computer work station. The case 4 is normally made of metal or plastic and is generally opaque. It may if desired have various access doors for access to the internal equipment or it may be simply mounted so as to be capable of being lifted off the base 6 for access to the interior.

At one end of the case 4 is a viewing screen 8 onto which the visual image can be projected, usually by rear projection. The screen 8 is preferably made sufficiently large in area that it encompasses a major portion of the patient/viewer's side 5 of the case 4, except for the lower panel 7 where the controls to be manipulated by the patient are located. The reason for this is that more accurate and consistent results are obtained from the tests if the patient does not see the screen as surrounded by a "border" or "frame." By extending the screen 8 completely across most of the patient's side 5 of case 4, and preferably also overlapping slightly into adjacent sides as at 9, only a single distinct edge is within the patient's vision, at the junction of screen 8 and panel 7, so the accuracy of the test is maximized. For the best results, the screen should subtend angles of approximately 40° horizontally and 30° vertically as viewed by the patient. Since the patient sits at a position where his or her eyes are approximately 50 cm (19.7") from the screen surface, the dimensions of the screen will therefore be approximately 36 cm wide by 27 cm high (14.2"×10.6").

The case 4 will also be perforated for passage of shafts 10, 12, 14 and 16 whose function will be described below.

Within the case 4 are means for producing two visual images, in this case exemplified by a common photographic type of projector 18, such as that used to project film slides. Projector 18 is controlled by off/on switch 19, which is placed in a conventional electrical power cord (not shown). In the embodiment illustrated the projector 18 projects a photographic light through lens 20 over which are placed a pair of filters 22 and 24, which will be further described below. In front of the lens 20 and filters 22 and 24 is an image creating member 26. Image creating member 26 may be any of a variety of articles containing one or more split images, and being structured that each of those split images can be separately projected onto screen 8. For instance, member 26 may be a slide/transparency, film strip, glass plate, glass disc or other device in the form of a sheet material which is transparent in at least its image area, and with the desired split image or images applied to its surface, etched or cut into its surface or incorporated into the sheet itself (as with a film). A particularly preferred member 26 is a flat plate or "stencil," generally opaque and commonly made of metal or heat resistant plastic, which has cut into it at least one split image with two opening portions and usually a plurality of pairs of such openings, for different split images. Of course each different type of member 26 will be held either fixed or rotatably by an appropriate support, as will be described below for the exemplified flat metal place of FIG. 3.

Regardless of the form of member 26, the two portions of each split image 28 (individually designated 28a and 28b) are aligned such that the light from projector 18 is split, with the light which passes through filter 22 also passing through opening 28a and the light which passes through filter 24 also passing through opening 28b. As best seen in FIG. 2, the resulting light rays 30 and 32 are focused by lens 34 (which may be a zoom lens), and then reflected by mirrors 36 and 38 respectively so as to present two upright images by rear projection on screen 8.

The member 26 (here exemplified by a metal disc) may conveniently be mounted on the shaft of a gear set 40 so that it can be rotated under the control of the examiner to allow different ones of the split images 28 to be projected on the screen 8. Movement of the gear set 40 is controlled by the examiner through manipulation of knob 42 at the end of shaft 14 which turns a conventional linkage 44 to move gears 40 and rotate disc 26. (Alternatively, gear set 40 could be replaced by a stepping motor and motor control switch.) Similarly, the focus, zoom and/or direction of lens 34 can be adjusted by the examiner by turning knob 46 attached to shaft 16.

This allows the examiner to assess various combinations of ocular coordination conditions in which the visual axes are not aligned in precise horizontal and vertical orientations.

In the embodiment shown in FIGS. 1 and 2, the image emerging from lens 34 is reflected from mirror 48 to mirrors 36 and 38. This is for convenience and compactness of the equipment within the case 4. Alternatively, the image emerging from lens 34 could be focused directly on the mirrors 36 and 38 without reflection, or additional mirrors or prisms could be placed in the light path to obtain the desired degree of compactness of the equipment. Those skilled in the optics art will be well aware of such use of mirrors and prisms in a light path and will be able to determine satisfactory combinations such that the resulting images are presented on screen 8 with the desired orientation and resolution and with sufficient brightness to enable the patient to observe the images clearly.

Figure 4:
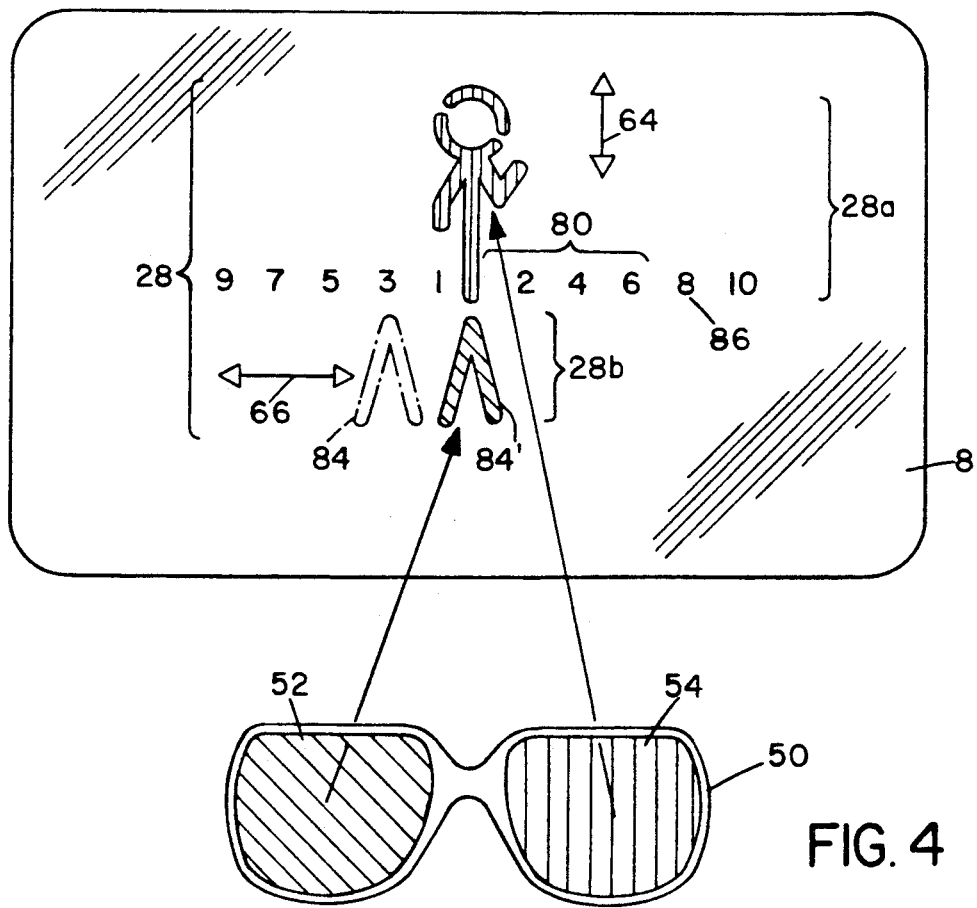
FIG. 4 illustrates a typical projected image showing the relationship of the isolating filters, here depicted as red and green viewing spectacles and a red and green image.

The filters 22 and 24 are selected in coordination with another pair of corresponding filters, which are shown in FIG. 4 as part of spectacles 50 which are to be worn by the patient during the examination. The lenses 52 and 54 in spectacles 50 in the embodiment are shown lined respectively for green and red color transmission. This corresponds respectively to equivalent red and green filters 22 and 24, such that as shown in FIG. 4 the image 28a appears in red and the image 28b appears in green. Since red and green are complimentary colors, the red portion 28a of the image on the screen will not be visible to the patient through the eye viewing the image through the green filter/lens 52 and the green portion 28b of the projected image will not be visible to the patient through the eye viewing the image through the red filter/lens 54. In other words, each of the patient's eyes is visually isolated and sees a different and mutually exclusive portion of the projected image 28. It will be recognized that the pair of filters 52 and 54 may be housed in other than a spectacle frame depending on the type of patient being assessed. For instance, the filters 52 and 54 may be made part of a stand-alone device with an opaque center dividing wall, the device being placed between the patient and the screen 8 with the wall isolating the individual eyes' vision Such a device might be used, for instance, where a patient cannot, perhaps because of injury, wear spectacles. All that is required is that whatever type of device 50 the patient looks through to view the screen 8, it must be such that the patient's line of sight from each eye is isolated and restricted such that each eye's line of sight goes through only a single one of the filters 52 and 54.

In FIG. 4 the spectacles 50 and the image 28 have been shown with respect to red/green color light separation. There are of course other types of visual separation means well known to those in the field, including blue/yellow color separation and polarized light separation. In the case of polarized light, the two filters 52 and 54 would be made of polarizing filters with axes crossed at 90° and the filters 22 and 24 would have corresponding crossed polarized axes.

Figure 5:
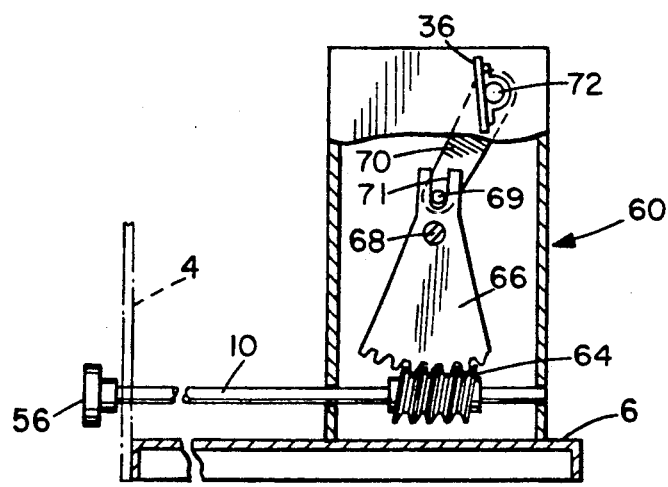
FIG. 5 is a side elevation view, partially cut away, of a mechanism for actuating one movable mirror.

Returning to FIG. 1, it will be seen that shafts 10 and 12, which terminate in knobs 56 and 58 respectively, are linked through linkages 60 and 62 to mirrors 36 and 38 respectively, thus permitting mirror 36 to be rotated in the vertical plane and mirror 38 to be rotated in the horizontal plane, so as to move the image portions 28a and 28b as indicated by arrows 63 and 65 in FIG. 4. Both linkages 60 and 62 are worm and cam drives best shown in FIGS. 5 and 6. For the vertical movement of mirror 36, the rotation of shaft 10 by knob 56 causes worm gear 64 to rotate gear segment 66 around pivot 68. Gear segment 66 is linked to lever 70 by pin 69 which moves in slot 71, with lever 70 in turn fixed to shaft 72 on which mirror 36 is mounted. Thus as the patient turns knob 56 and rotates shaft 10 in worm 64, the resulting movements of gear segment 66 and lever 70 causes shaft 72 to be rotated and mirror 36 to move as indicated by arrow 74.

Figure 6:
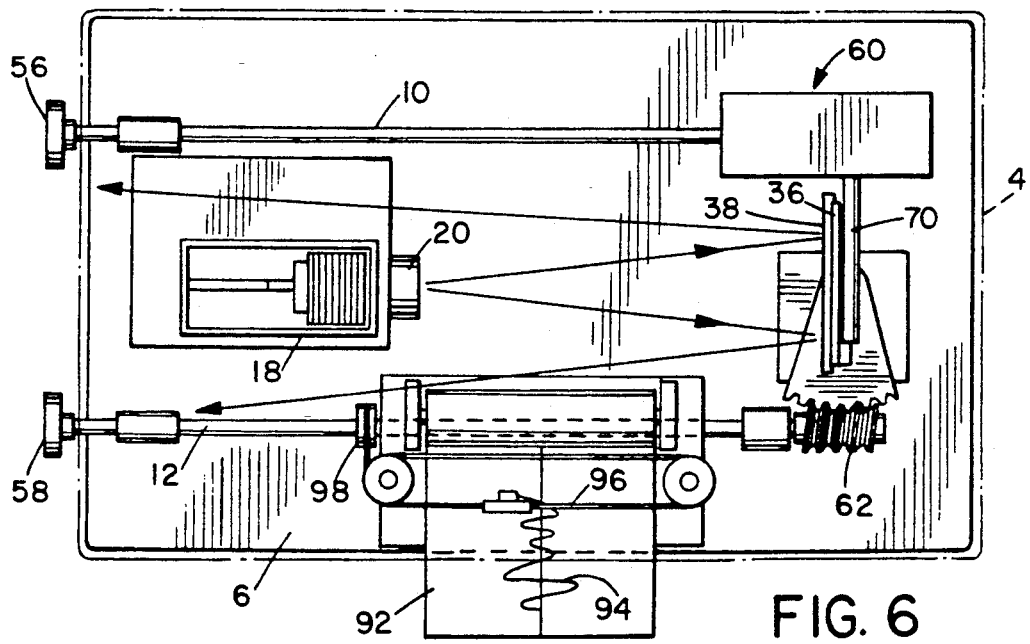
FIG. 6 is a top plan view of an alternative unit using a slide projector for projecting images and a graphic motion recorder.

Similarly, as best seen in FIGS. 1 and 6, rotation by the patient of knob 58 to rotate shaft 12 and worm 76 causes movement of gear segment 78 and shaft 80 to which it is attached, thus causing rotation of mirror 38 as indicated by arrow 82.

Figures 9A, 9B:
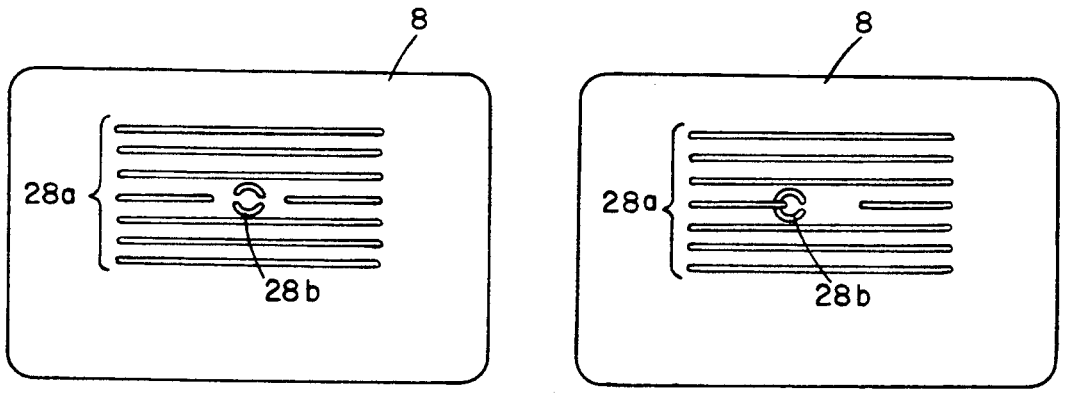
FIGS. 9A and 9B illustrate, respectively, aligned and misaligned split images of another type.

The method of this invention for quantitative assessment of the patient's ocular coordination follows from the preceding description. At the beginning the examination, the patient dons the spectacles 50 with the mutually exclusive lenses 52 and 54. The examiner then selects a particular image pair 28 and aligns that pair on disc plate 26 with the light emerging from filters 22 and 24. In normal practice, the examiner will previously have adjusted knobs 56 and 58 such that the resulting portions 28a and 28b of the split image 28 as viewed on screen 8 are offset from accurate alignment, as is illustrated in FIGS. 4, 9A, and 9B, either or both vertically and horizontally. The test then consists of having the patient, who is looking through the spectacles 50, bring the two image portions 28a and 28b into what the patient views as correct alignment. For instance, in the example shown in FIG. 4, the image portion 28a consists of the body and head portion of a simple stick person figure, along with a calibrated numerical scale. The lower portion 28b consists of legs of the stick figure which are initially shown as being misaligned at 84. The patient then manipulates the control (in this case knob 58) to move the image portion 28b to bring the stick figure legs into alignment 84' with the body and head portion of the figure, as viewed by the patient. Once the patient has aligned the figure correctly as he or she sees it, the patient stops manipulating the controls and the examiner then views the combined image 28 as it appears on the screen 8. Since the examiner is of course viewing the image 28 without any obstructing filters 52 and 54, the examiner sees the complete figure in its true alignment and can determine the degree of separation between the two portions of the figure by comparison of the position of the portion 28b with respect to the numerical scale 86. For instance, if the patient during manipulation of the knob 58 had considered that the figure was properly aligned as he or she viewed it through the spectacles 50 when in fact the leg portion 28b was in the position indicated at 84, the examiner can then tell that the patient's coordination was off by a value of 3 units to the left of the correct orientation as indicated by scale 86.

In a preferred embodiment, the scale 86 as illustrated in FIG. 4 is divided into prism diopter units with the positive diopter units to the right and the negative diopter units to the left. Alternatively, the scale may be a proportionate scale which is convertible into prism diopter units. Right displacement corresponds to exophoria and left displacement corresponds to esophoria. It has been found by experimentation that patients whose test results fall within the portion 81 of the diopter scale 86 in FIG. 4 which represents 0 to +6 prism diopter units do not need visual correction, whereas those who results fall on the negative diopter side of the scale 86 or with a positive difference of greater than +6 diopter units will normally require some type of corrective lenses.

Figure 3:
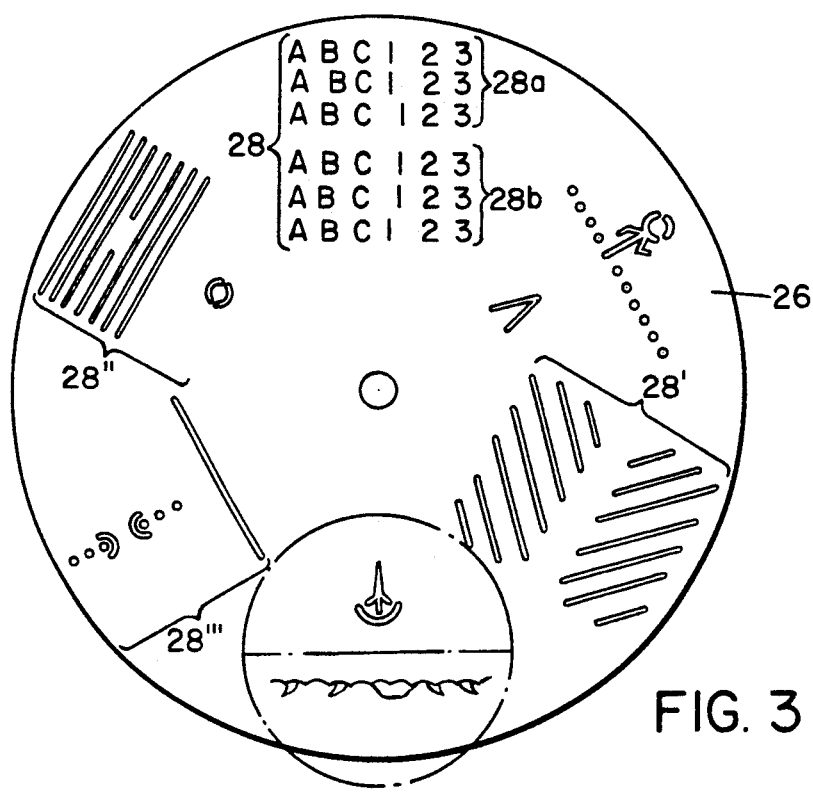
FIG. 3 is a rear face view of a multiple image disc.

The split images 28 may be of a variety of different types, selected both relative to the condition being assessed and also by the age and ability of the patient. It is important, however, that the images be chosen so that the viewer's brain will not resolve the binocular input by subconsciously "fusing" the two portions of the split image, into a single image, even when the portions are overlapping. Normally this means that the two portions should contain at least about 50% non-congruent elements, both in color and in graphic association. For instance, if the split image is of the separated letters of a common word, such as having the spaced apart letters C, I, A, and O form one image portion 28a and the letters H, C, and G form the other interspersed portion 28b, the patient will try to form what he or she believes to be a correctly spaced appearance of the word "CHICAGO". However, since the word "CHICAGO" is well known to many patients, there is an inherent tendency for the brain to form a fused image which is not truly representative of the patient's visual condition. Similarly, a triangle and a square often cause the viewer to fuse the two into a simple "house" image. If there are a majority of non-congruent elements, however, the images are such that the two halves do not form a figure or word which the brain tends to fuse. Thus, as illustrated in FIG. 3, the opposed diagonal lines 28', the lines and circle 28" and the C's, dots and line 28''', all form images which do not cause fusion. An alternative way of avoiding fusion is to design an image to incorporate deliberate misalignments, so that the tendency of the brain to cause fusion is thwarted, since the portions of the image will not properly fuse. For instance, in FIG. 3 the image 28 made up of the letters A, B and C and the numerals 1, 2 and 3 will be seen to have several numbers and letters out of alignment with their neighbors. These misaligned characters cannot be fushed with their opposite characters in the other portion of the image, producing instead a "3-D" effect, so the patient's alignment of the two portions of the image gives a true indication of his or her visual condition, free of fusion.

Other types of typical images 28 which can be used are shown in FIGS. 3, 7A-7B, 8 and 9A-9B. For instance, in FIGS. 9A and 9B, the object is for the patient to position the circle 28b in the center of the opening in the grid 28a. The degree to which the patient misaligns the two portions 28a and 28b is a direct quantitative indication of the degree of severity of the patient's lack of ocular coordination. Of course, numerous other types of image pairs can also be used.

Figure 8:
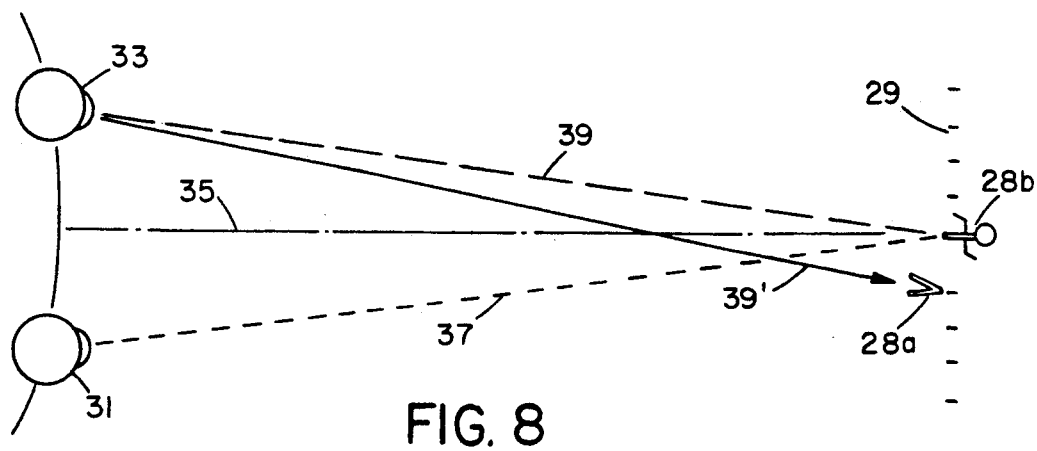
FIG. 8 illustrates schematically a method of detecting lateral deviation in one of a patient's eyes.

FIG. 8 represents use of the system to enable the eye care professional to easily identify and diagnose a permanent deviational condition or dysfunction of one eye, which has in the past been extremely difficult to detect and particularly to quantify. If the patient can consistently properly center one portion 28b of the split image 28 with respect to the eyes' centerline 37 and the scale 29, while consistently placing the other portion 28a out of center alignment, the examiner can tell that one eye (here the right eye 31) is properly focused along line of sight 37 while the other eye (here the left eye 33) has a deviation of the proper line of sight 39 to the deviated position 39'. Which eye is deviant is immediately apparent, and a simple calculation based on the degree of deviation shown on the scale 29 and the distance of the patient's eyes from the screen will provide a precise measure of the degree of deviation.

Figure 7A:
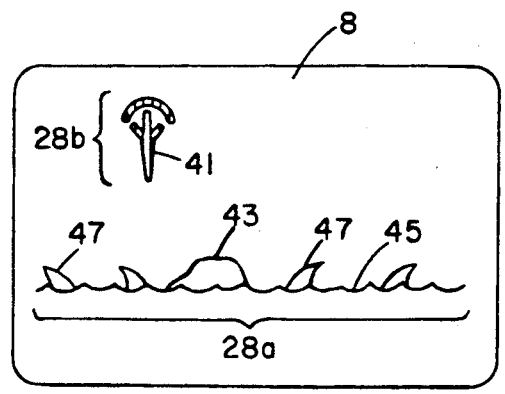
FIGS. 7A and 7B illustrate, respectively, misaligned and correctly aligned split images.
Figure 7B:
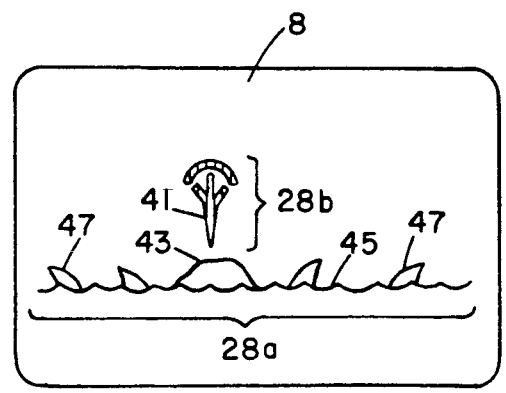

It will be evident that the pairs of images 28 in FIGS. 4, 9A and 9B can also be manipulated vertically as indicated by the arrow 63 in FIG. 4. A typical illustration of a vertical alignment test is shown in FIGS. 7A and 7B, where the patient's task is to align the little parachutist FIG. 41 with the island 43, and avoid the sea 45 full of sharks 47. The degree to which the parachutist FIG. 41 is misaligned with the island 43 is the measure of the patient's vertical coordination. I have found that images such as those shown in FIGS. 7A and 7B as well as that of FIG. 4 are particularly useful for the testing of children. Often it is difficult to hold a child's attention during a prolonged testing session with conventional images, but the use of cartoon-like images such as the island, sharks and parachutist in FIGS. 7A and 7B normally catch the child's fancy. The examiner, by relating to the child a narrative involving the parachutist trying to escape the sharks and land on the island, can get the child to willingly and eagerly participate in the test. This type of test works better with children than an image such as the image 28 shown in FIG. 3 if the child is too young to be able to recognize letters. It is also quite useful for testing adults who may be illiterate or are from a foreign culture and do not recognize alphabetical characters of the examiner's language.

Figure 10:
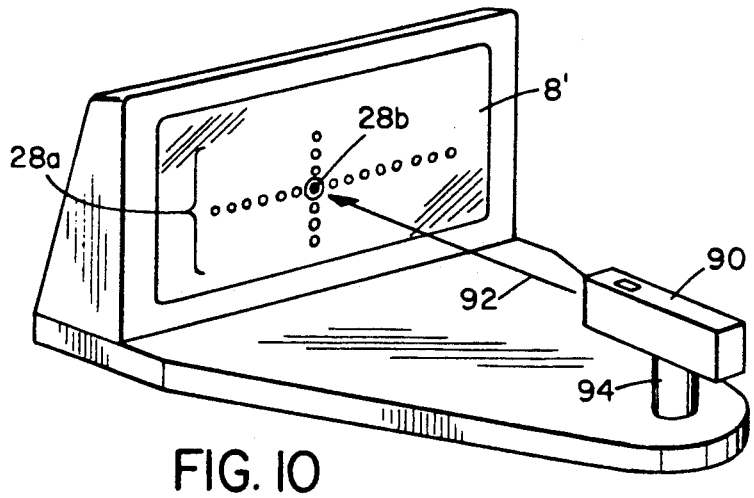
FIG. 10 illustrates an alternative apparatus using a split image having one portion stationary and the other portion projected by a laser and movable in (x,y) coordinates.

Another embodiment of the invention is shown in FIG. 10. In this embodiment, a single portion of the image 28 (portion 28a; here shown as a crossed pattern reticle) is projected, usually by rear projection, on the screen 8'. The second portion of the image 28 (portion 28b; in this case a dot) is generated by a laser 90 and projected against the screen 8' as indicated at 93. The laser 90 is mounted on post 95 such that it can pivot both horizontally and vertically. During the test, the patient, while viewing the screen through spectacles 50, manipulates the laser so as to position the image portion 28b in what he or she visualizes to be the correct orientation with respect to portion 28a on the screen 8. At the termination of the test, the examiner and patient can immediately observe where the image 28b is actually placed with respect to image portion 28a and thus quantitatively determine the patient's degree of lack of ocular coordination or dysfunction.

Figure 12:
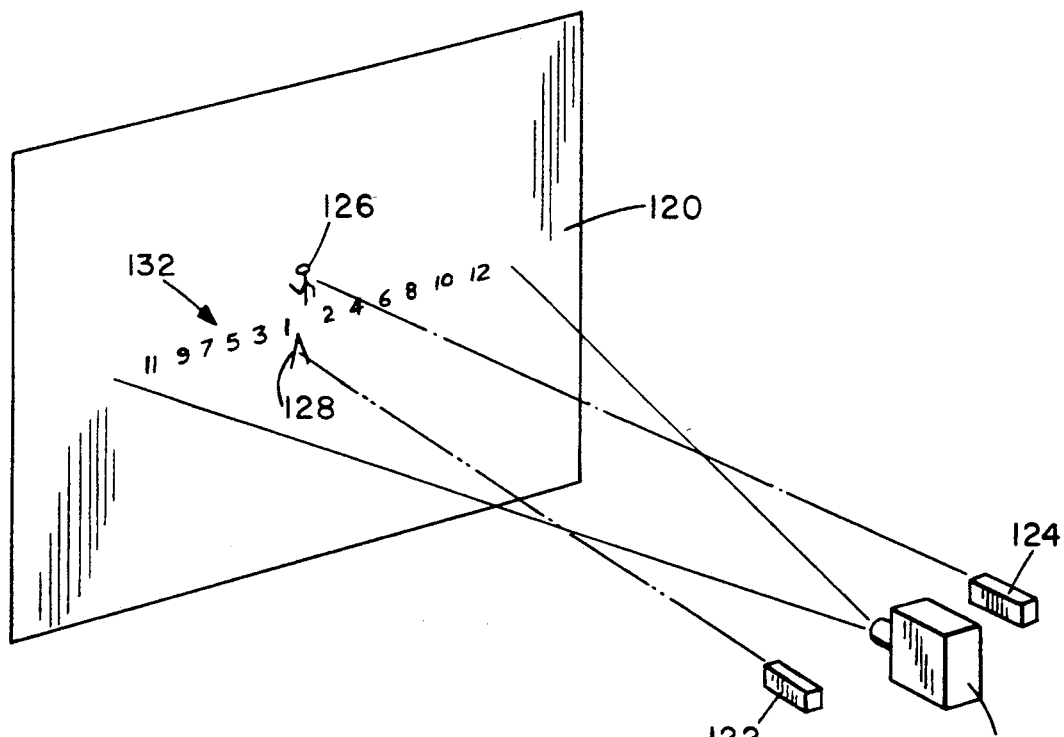
FIG. 12 illustrates an embodiment in which the images are front-projected rather than rear-projected.

A variation of this embodiment is illustrated in FIG. 12, which utilizes a front projection surface 120, such as a movie screen or a flat wall. This embodiment uses two light projecting guns 122 and 124, each of which projects one of the two half images (respectively 128 and 126) of the split image onto the surface 120. One or both of these two guns can be manipulated by the patient. Also included is a projector 130 which projects the scale 132 onto the surface 120. The patient then manipulates one or both of the guns 122 and 124 to move the images on the surface 120 against the scale 132 until they appear to him or her to be aligned, in the manner described above.

Figure 11:
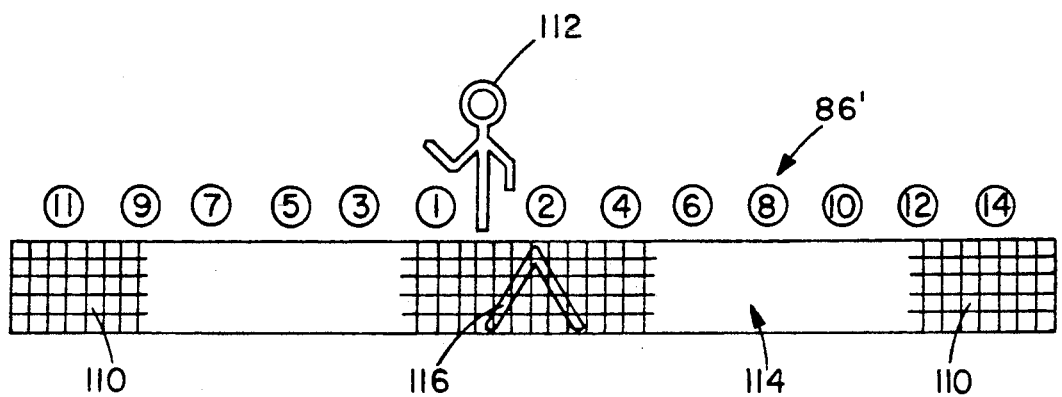
FIG. 11 illustrates an embodiment in which the contrasting color regions are created by use of light emitting diodes.

In yet another embodiment of the invention, illustrated in FIG. 11, one uses a matrix 114 of one color of light emitting diodes (LED's) 110 with the color approximately matching a color of one of the filters in the spectacles. One-half 112 of the split image is formed adjacent to LED matrix 114 in the complimentary color (matching the other spectacle filter color); this half image 112 may be formed by LED's or other means. The other half 116 of the split image is formed in the matrix 114 and moved electronically by having the appropriate LED's turned on or off in the matrix. A scale 86' is also normally formed on the screen for observation by the examiner. This embodiment is particularly important for use in conjunction with an automated refractor system which incorporates this invention. In such an automatic system the output of the LED's 110 is digitized to identify the location of the half image 116 in the matrix 114. These data are automatically processed by an associated computer for comparison with the location of the half image 116, so that the patient data (and perhaps ultimately diagnoses) can be rapidly and automatically generated. In the automated embodiment the scale 86' may be optional, since an equivalent calibration may be part of the computer's analysis programming.

It will be immediately apparent that the devices and examining technique of the present invention provide a very simple, accurate and reproducible manner of obtaining a precise quantitative assessment of a patient's ocular coordination. By simple selection of the particular image pair 28 chosen, the eye care professional can present tests which are easily performed and understood not only by literate adults, but also by those unfamiliar with the examiner's language and those such as small children who are unable to articulate image description accurately and/or attention is normally easily diverted from participation in lengthy eye tests.

Further, the tests can be reproduced with virtually identical results time and time again, since there is no reliance upon the patient's verbal description of the scene but rather merely direct observation by the examiner of the precise relationship of the two parts of the image which are created by the patient's manipulation of the device controls. It has been found in extensive experimentation that patients normally reproduce essentially the same relationship for a given image pair in repeated performances of the tests, even where the repetitions of the image pair are widely spaced apart in time.

It will also be seen that the invention readily lends itself to standard calibration such that each patient's own individual alignment of a given image can be immediately compared to a standard calibration of the equipment, such that the correct prescription of corrective lenses for a patient can be readily and promptly made.

It will also be evident that the present invention can be easily operated by a trained technician as well as by the eye care professional, since there is no interpretative aspect to the observation of the patient's test. In other words, the technician need only to observe and measure the physical location of the two image portions 28a and 28b when the patient completes each test and does not need to try to make any interpretation of a subjective verbal description of an image as seen by the patient. Thus a technician or optical assistant can conduct the test, record the results in numerical form and present them to the eye care professional for the latter's interpretation and prescription of any necessary corrective lenses. This of course is a much more efficient use of the professional's time than having to conduct lengthy tests directly.

Similarly, such tests could be used in schools by trained technicians, to identify children with apparent ocular coordination problems who could then be referred to appropriate eye care professionals for a thorough examination. Currently schools now use only conventional wall eye charts, which only detect visual acuity. Use of the present test in conjunction with the standard eye chart test would be much more effective than use of the eye chart alone, since the combination provides important information about the child's vision which cannot be obtained from the eye chart alone. The fact that this test does not depend on the child's recognition of letters or symbols from the chart or on the child's subjective narrative of how he or she views the letters or symbols on the chart also is advantageous, particularly for testing young children in their early years of school or pre-school. Such school tests can also incorporate a permanent record of the test into the child's file.

With respect to permanent records, it will be noted that FIG. 6 illustrates a version of the invention in which the manipulation of shaft 12 also drives a recording chart 92 on which the manipulation of the knob 58 by the patient causes recording of the movement of the image portion 28a by the recorded trace 94 through a cable linkage 96 which is attached to shaft 12 by sheave 98. A conventional motor drive (not shown) feeds the recording paper 92 at a predetermined rate. When the patient has the image aligned visually correctly as perceived by him or her through the spectacles 50, the motor drive is stopped and recording trace 94 will provide a permanent record of that alignment, which can be used either for a permanent record in the patient's file or for instruction purposes where the device is in use at a teaching facility. A similar drive and recording structure can be mounted on shaft 10 to make a permanent record vertical alignment changes made by the patient.

It should be noted that the horizontal alignment is often considered the more important in most cases of lens prescription, since a significant majority of the patients who have ocular coordination dysfunctions have the principal lack of coordination in the horizontal plane. While there may be found some degree of lack of vertical coordination, this is usually the result of physical problems that cause ocular dysfunctions which can result in vertical disorientation. Thus vertical measurements may be of significance in assessing a patient's physical condition since the vertical disorientation may be due to medical or physical factors other than actual eye problems. Thus one can to some extent consider that vertical displacement is of medical significance because it suggests the presence of some physical abnormality, while horizontal displacement is more commonly of visual significance, since it determines conditions that can be corrected by prescription lenses and is related to the most common muscle balance disorder.

The present invention is particularly useful for assessing lack of depth perception, degree of muscle balance between the eyes, individual eye dominance and rivalry, and other aspects of binocular coordination. It will also be evident that the device is quite simple and compact, such that it is easily located and used in the typical eye care professional's office and can be used with a wide variety of patients. Incorporation of the recording feature shown in FIG. 6 also makes possible the collection of permanent examples of various degrees of disorientation so that these can be used by students to learn the significance of the various possible orientations and relationships between the image portions without having to actually conduct a series of experiments each time the professional student's training is undertaken. Also, the ability to prepare such records allows the eye care professional who encounters a particularly unusual case to present those results to professional colleagues in the form of professional papers or the like, such that the eye care profession can enjoy the benefits of such research and learn to recognize such types of unusual cases in the future.

It will be evident that there are numerous embodiments of this invention which, while not expressly described above, are clearly within the scope and spirit of the invention. The above description is therefore intended to be exemplary only, and the scope of the invention is to be limited solely by the appended claims.

I claim:

1. Apparatus for quantitative assessment of human ocular coordination, which comprises:
   a first pair of transparent image filters, each filter of said first pair having means to transmit a visual image different from and mutually exclusive with the image transmitted by the other filter of said pair;
   means for producing a pair of visual images and displaying them on a viewing surface;
   said viewing surface on which said visual images are presented to a human patient, each visual image being visible to said patient through only one respective filter of said pair of filters;
   means for said patient to move one of said visual images relative to the other on said viewing surface; and
   means for quantitatively determining the spatial relationship between said visual images on said viewing surface which results from movement of said one of said visual images by said patient.

2. Apparatus as in claim 1 further comprising:
   a second pair of transparent image filters, each filter of said second pair having means to transmit a visual image different from and mutually exclusive with the image transmitted by the other filter of said second pair but corresponding to the image transmitted by one respective filter of said first pair; and
   means for projecting each of said pair of visual images through a respective one of said second pair of filters and onto said viewing surface.

3. Apparatus as in claim 2 wherein said means for producing said images comprises a light projector with its output light directed to a stencil comprising a generally opaque plate having two openings therethrough, that portion of said light passing through said openings forming said pair of images on said viewing surface.

4. Apparatus as in claim 3 wherein that portion of light passing through one of said openings also passes through one filter of said second pair of filters, and that portion of light passing through the other of said openings also passes through the other filter of said second pair of filters.

5. Apparatus as in claim 1 wherein said first pair of filters is in the form of spectacles worn by said patient in which each filter is positioned in front of a respective one of said patient's eyes.

6. Apparatus as in claim 1 wherein said filters of said first pair differ from each other in their ability to transmit colored light.

7. Apparatus as in claim 6 wherein the wavelengths of the respect colored lights transmitted by said filters of said first pair are such that the colors are complementary and mutually cancelling visually.

8. Apparatus as in claim 7 wherein one of said filters transmits predominately green light and the other of said filters transmits predominately red light.

9. Apparatus as in claim 7 wherein one of said filters transmits predominately yellow light and the other of said filters transmits predominately blue light.

10. Apparatus as in claim 1 wherein said filters of said first pair differ from each other in their ability to transmit polarized light.

11. Apparatus as in claim 10 wherein one of said filters transmits predominately light polarized at right angles to the light predominately transmitted by said other filter.

12. Apparatus as in claim 1 wherein said pair of images comprise the two portions of a split image.

13. Apparatus as in claim 12 wherein said pair of images are selected such that they do not promote visual fusion by said patient.

14. Apparatus as in claim 13 wherein said images have less than 50% congruent elements.

15. Apparatus as in claim 1 wherein said viewing surface is a rear projection screen.

16. Apparatus as in claim 1 wherein said viewing surface is a front projection surface.

17. Apparatus as in claim 1 wherein said means for producing said images comprises a light projector with its output light directed to a stencil comprising a generally opaque plate having two openings therethrough, that portion of said light passing through said openings forming said pair of images on said viewing surface.

18. Apparatus as in claim 17 wherein said plate has therein a plurality of pairs of openings, each pair corresponding to a desired one of pair of said images, said plate being adapted to be moved such that said output light can be directed through different respective pairs of openings on said plate to present different pairs of images on said viewing screen.

19. Apparatus as in claim 1 wherein said means for producing said images comprises a light projector with its output light directed through a transparent sheet material which has at least one of said pair of images incorporated therewith, with said light passing through said transparent sheet material and projecting said pair of images onto said viewing surface.

20. Apparatus as in claim 19 wherein said transparent sheet material comprises film, slide transparency or glass.

21. Apparatus as in claim 1 wherein said means for producing said pair of images comprises two separate image producing devices, each of which produces a respective one of said pair of images.

22. Apparatus as in claim 1 wherein said means for quantitative determination of said spatial relationship comprises a predetermined numerical scale displayed on said viewing surface.

23. Apparatus as in claim 22 wherein said numerical scale is calibrated in prism diopter units.

24. Apparatus as in claim 22 wherein said numerical scale is a proportional scale which is convertible into prism diopter units.

25. Apparatus as in claim 1 wherein said means for quantitative determination of said spatial relationship comprises means for observing the alignment of respective predetermined portions of each of said images.

26. Apparatus as in claim 1 wherein said means for producing said visual images comprises a photographic light projector.

27. Apparatus as in claim 1 wherein said means for producing said visual images comprises an optical laser.

28. A method for quantitative assessment of human ocular coordination, which comprises:
producing a pair of visual images;
displaying said pair of visual images to a human patient on a viewing surface, each visual image being visible to said patient through a first pair of transparent image filters, each filter of said first pair having means to transmit a visual image different from and mutually exclusive with the image transmitted by the other filter of said pair such that said patient sees each image through only one respective filter of said pair of filters;
providing means for said patient to move one of said visual images relative to the other on said viewing surface; and
quantitatively determining the spatial relationship between said visual images on said viewing surface which results from movement of said one of said visual images by said patient.

29. A method as in claim 28 further comprising:
providing a second pair of transparent image filters, each filter of said second pair having means to transmit a visual image different from and mutually exclusive with the image transmitted by the other filter of said second pair but corresponding to the image transmitted by one respective filter of said first pair; and
projecting each of said pair of visual images through a respective one of said second pair of filters and onto said viewing surface.

30. A method as in claim 28 wherein said filters of said first pair differ from each other in their ability to transmit colored light.

31. A method as in claim 30 wherein the wavelengths of the respective colored lights transmitted by said filters of said first pair are such that the colors are complementary and mutually cancelling visually.

32. A method as in claim 31 wherein one of said filters transmits predominately green light and the other of said filters transmits predominately red light.

33. A method as in claim 31 wherein one of said filters transmits predominately yellow light and the other of said filters transmits predominately blue light.

34. A method as in claim 28 wherein said filters of said first pair differ from each other in their ability to transmit polarized light.

35. A method as in claim 34 wherein one of said filters transmits predominately light polarized at right angles to the light predominately transmitted by said other filter.

36. A method as in claim 28 wherein said quantitative determination of said spatial relationship is obtained by observation of the relation of said images to numerical scale displayed on said viewing surface.

37. A method as in claim 36 wherein said numerical scale is calibrated in prism diopters.

38. A method as in claim 36 wherein said numerical scale is a proportional scale which is convertible into prism diopter units.

39. A method as in claim 28 wherein said quantitative determination of said spatial relationship is obtained by observation of the alignment of respective predetermined portions of each of said images.

* * * * *

UNITED STATES PATENT AND TRADEMARK OFFICE
CERTIFICATE OF CORRECTION

PATENT NO. : 5,309,185
DATED : MAY 3, 1994
INVENTOR(S) : GILBERTO B. HARPER

It is certified that error appears in the above-indentified patent and that said Letters Patent is hereby corrected as shown below:

- Column 12, line 63, delete "respect" and insert

--respective--.

Signed and Sealed this

First Day of November, 1994

*Attest:*

*Attesting Officer*

BRUCE LEHMAN

*Commissioner of Patents and Trademarks*